US012569289B2

(12) United States Patent
Pozzato et al.

(10) Patent No.: US 12,569,289 B2
(45) Date of Patent: Mar. 10, 2026

(54) ELECTRONIC DEVICE FOR BIOMEDICAL USE IMPLEMENTING QMR TECHNOLOGY

(71) Applicant: Telea Medical Group S.R.L., Sandrigo (IT)

(72) Inventors: Gianantonio Pozzato, Vicenza (IT); Alessandro Pozzato, Vicenza (IT)

(73) Assignee: Telea Medical Group S.R.L., Sandrigo (IT)

( * ) Notice: Subject to any disclaimer, the term of this patent is extended or adjusted under 35 U.S.C. 154(b) by 302 days.

(21) Appl. No.: 18/552,710

(22) PCT Filed: Jul. 6, 2022

(86) PCT No.: PCT/IB2022/056240
§ 371 (c)(1),
(2) Date: Sep. 27, 2023

(87) PCT Pub. No.: WO2023/281412
PCT Pub. Date: Jan. 12, 2023

(65) Prior Publication Data
US 2024/0164828 A1 May 23, 2024

(30) Foreign Application Priority Data
Jul. 6, 2021 (IT) ........................ 102021000017783

(51) Int. Cl.
*A61B 18/12* (2006.01)
*A61B 18/14* (2006.01)

(52) U.S. Cl.
CPC .......... *A61B 18/1206* (2013.01); *A61B 18/14* (2013.01); *A61B 2018/128* (2013.01)

(58) Field of Classification Search
CPC ..... A61B 18/12; A61B 18/1206; A61B 18/14; A61B 2018/128
See application file for complete search history.

(56) References Cited

U.S. PATENT DOCUMENTS

| | | | | |
|---|---|---|---|---|
| 7,571,003 B2* | 8/2009 | Pozzato | ............. | A61B 17/3211 |
| | | | | 607/69 |
| 2017/0354818 A1* | 12/2017 | De Toni | ............... | A61N 1/0484 |
| 2019/0133681 A1* | 5/2019 | Jeong | ................. | A61B 18/0206 |

FOREIGN PATENT DOCUMENTS

| | | |
|---|---|---|
| EP | 1 087 691 B1 | 5/2002 |
| EP | 3 349 848 A1 | 7/2018 |

(Continued)

OTHER PUBLICATIONS

International Search Report and Written Opinion dated Nov. 2, 2022, issued in PCT Application No. PCT.IB2022/056240, filed Jul. 6, 2022.

(Continued)

*Primary Examiner* — Michael F Peffley
(74) *Attorney, Agent, or Firm* — Workman Nydegger

(57) ABSTRACT

An electronic device for biomedical use includes a radio frequency circuit which can be powered by a voltage and at least one electrode connected at the output to the radio frequency circuit and applicable to a part of a person's body. The radio frequency circuit is configured to generate as output an electric current wave with fundamental frequency higher than or equal to 2 MHz and distorted by the presence of at least second-order harmonics, wherein the first percentage ratio between the amplitude of the peak of the electric current wave at the second-order harmonic and the amplitude of the peak of the electric current wave at the fundamental frequency is comprised between 20% and 70% when a load around 100 Ohms is applied to the electrode, whereas said first percentage ratio is comprised between 25% and 120% when a load around 830 Ohms is applied to the electrode.

13 Claims, 3 Drawing Sheets

(56) References Cited

FOREIGN PATENT DOCUMENTS

| | | | |
|---|---|---|---|
| EP | 3 616 632 | A1 | 3/2020 |
| WO | 2004/108211 | A1 | 12/2004 |

OTHER PUBLICATIONS

Giulio Ferrari et al., *High Frequency Electrotherapy for the Treatment of Meibomian Gland Dysfunction*, Clinical Science, vol. 38, No. 11, Nov. 2019, pp. 1424-1429.

Marco Dal Maschio et al., *Biophysical Effects of High Frequency Electrical Field (4-64 MHz) on Muscle Fibers in Culture*, Basic and Applied Myology, vol. 19, No. 1, 2009, pp. 1-9.

* cited by examiner

ELECTRONIC DEVICE FOR BIOMEDICAL USE IMPLEMENTING QMR TECHNOLOGY

BACKGROUND OF THE INVENTION

1. The Field of the Invention

The present invention concerns an electronic device for biomedical use implementing QMR technology.

2. The Relevant Technology

It is known in physiology that the passage of electric currents, or rather electric fields, through biological tissues, in addition to generating thermal effects, is capable of modifying the distribution of the surface charges in cell membranes. Such variations in the charge distribution can induce modifications of membrane proteins and, among them in particular, the opening or closing of voltage-dependent ion channels.

At certain intensities, electric currents are able to cause electroporation in the membranes, enabling the transfer of molecules, even relatively large ones, across the membrane itself.

The effects of current on membrane potential may subsequently trigger important biological responses, such as pain control with low-frequency currents, or improvement of trophism and muscle performance.

In particular, it was demonstrated by the Applicant that the application of current waves with fundamental frequency higher than 2 MHz and distorted by the presence of harmonics transmits an energy to the molecules on which these current waves are applied that corresponds to the so-called "molecular resonance", known as the Quantum Molecular Resonance (QMR).

As reported in document EP1087691, this QMR energy is just enough to break the bonds among the molecules involved in the passage of current, making it particularly useful when applied, for example, to a scalpel. In particular, such molecular resonance advantageously makes it possible to limit the temperature increase of the tissues on which such electric fields are applied.

The QMR scalpel is in fact able to cut the regions of interest, without producing any effect of either rupture, tearing, necrosis, decrease or increase in thickness, alteration of fluid content, or other degenerative effect, around the cut.

More recent studies, such as that by Dal Maschio et al. (Biophysical effects of high-frequency electric field (4-64 MHZ) on muscle fibers in culture, BAM, 2009) also demonstrated how the effect on QMR-treated cells can depend on the frequency of the electric current waves in the QMR ranges and on the harmonic spectrum of the same waves.

Depending on the frequency used and the harmonic spectrum, the application of electric fields can in fact induce the deformation of the plasma membrane, leading, for example, to cell damage or stimulation of the treated cells.

In particular, Dal Maschio et al. demonstrated that the application of high-frequency electric fields in excitable type cells, such as muscle cells, generates a cellular response even when the threshold for the action potential is not reached, inducing the activation of intracellular signalling pathways even though the treated cell does not contract.

Further, Ferrari et al. (High Frequency Electrotherapy for the Treatment of Meibomian Gland Dysfunction, Clinical Science, 2019) showed how the application of QMR to patients with Meibomian Gland Dysfunction significantly reduces the symptoms and signs associated with the pathology, thus hypothesising its relevant role in the treatment of evaporative dry eye.

Yet another unpublished study showed how the application of QMR on glioblastoma multiforme cells reduces mitosis, motility and aggressiveness of these tumour cells, decreasing their ability to migrate through matrices to give rise to, for example, metastasis.

From these studies, it is therefore clear that the application of QMR to cells of different types can induce biological responses, even completely different from one another.

Not only that, but the application of QMR in cells of the same type but at different frequencies and, above all, with different harmonic spectra can also induce cell stimulations having biological effects and/or causing the activation of completely different cell pathways, as shown by Dal Maschio et al.

This discovery makes it possible to "modulate" the cellular function to obtain various biologically correct and functional functions.

In fact, the Applicant has discovered that by suitably changing the ratios between the harmonics constituting the QMR wave, in particular the distorted sinusoidal wave, it is possible to generate specific "cellular codifications" to obtain the desired function, for example tissue regeneration by acting on adult stem cells so as to obtain an effective cure for various musculoskeletal pathologies or a cure to counteract tumours or even a cure for tinnitus. The suitably modulated electric current wave QMR can also be effective in aesthetic medicine (rejuvenation medicine) or for other types of pathologies hitherto treated with invasive, insufficient and not long-lasting, but only temporary methods.

SUMMARY OF THE INVENTION

It is therefore necessary to identify those parameters relating to QMR electric currents which, by varying, can induce such different biological effects depending on the cells or tissues treated and thus depending on the Ohmic load applied to the device configured to generate such QMR currents.

Advantageously, the Applicant has recently identified the fundamental characteristics of the QMR electric currents that enable to modulate some of the desired biological effects on treated tissues or cells, even of a different type.

Based on this information, it is therefore an object of the present invention to develop an electronic device adapted to generate a plurality of electric currents in the range of the QMR frequencies and also that is configured to modulate such currents depending on the cells and tissues to be treated and/or on the biological effects to be obtained, and therefore depending on the Ohmic load applied to the device configured to generate such currents.

It is also an object of the present invention that such an electronic device be configured to modulate the electric currents generated based on the biological effect to be obtained on cells or tissues of the same type and on cells or tissues of a different type.

It is still an object of the present invention that such a device is configured to generate such electric currents without simultaneously causing a thermal effect on the treated cells or tissues.

Furthermore, it is an object of the present invention that such a device is configured to modify in real time and independently one or more of the parameters of the electric currents generated on the basis of the cellular or tissue response received, and therefore depending on the Ohmic load applied to the aforesaid electronic device.

It is also an object of the present invention that such a device has a good safety profile.

The above-mentioned objects are achieved by an electronic device for biomedical use, as set out in the claims.

In particular, the electronic device for biomedical use according to the invention comprises a radio frequency circuit powered by an appropriate voltage preferably of a continuous type, at least one electrode connected at the output to the radio frequency circuit and applicable on a person's body, in particular on the skin or on the internal tissues, wherein the radio frequency circuit is configured to generate as output an electric current wave with fundamental frequency higher than or equal to 2 MHZ, preferably at 4 MHz, distorted by the presence of at least the second-order harmonic, and wherein the percentage ratio, defined hereafter as the first percentage ratio, between the amplitude of the peak of the current wave at the frequency of the second-order harmonic and the amplitude of the peak of the current wave at the fundamental frequency is comprised between 20% and 70%, when an Ohmic load around 100 Ohms is applied to the electrode, whereas said first percentage ratio is comprised between 25% and 120%, when an Ohmic load around 830 Ohms is applied to the electrode.

Preferably, the aforesaid current wave has a sinusoidal shape distorted by at least the aforesaid second-order harmonic.

These particular values of the aforesaid first percentage ratio between the amplitudes of the peaks of the current wave relating to the second-order harmonic and to the fundamental frequency, depending on the applied load, make it possible, advantageously, to modulate some of the biological effects obtained with the application of QMR, and thus of the treatment to be carried out on the tissues or on the cells, even of a different type.

In particular, some of the possible treatments that can be carried out with the aforesaid electronic device for biomedical use of the invention, implementing the aforesaid QMR, concern, in a non-exclusive manner, the fields of surgery, ophthalmology, treatment of major wounds, aesthetic medicine, physiotherapy, tissue regeneration, tinnitus and cancer therapy.

Further characteristics of the device are described in the dependent claims.

BRIEF DESCRIPTION OF THE DRAWINGS

The aforesaid objects, together with the advantages that will be mentioned below, will be better highlighted during the description of some technical details of the device of the invention and of some application examples of the invention that are given, by way of non-limiting example, with reference to the attached drawing tables, where.

PRESENTATION OF THE INVENTION

Figure 1:
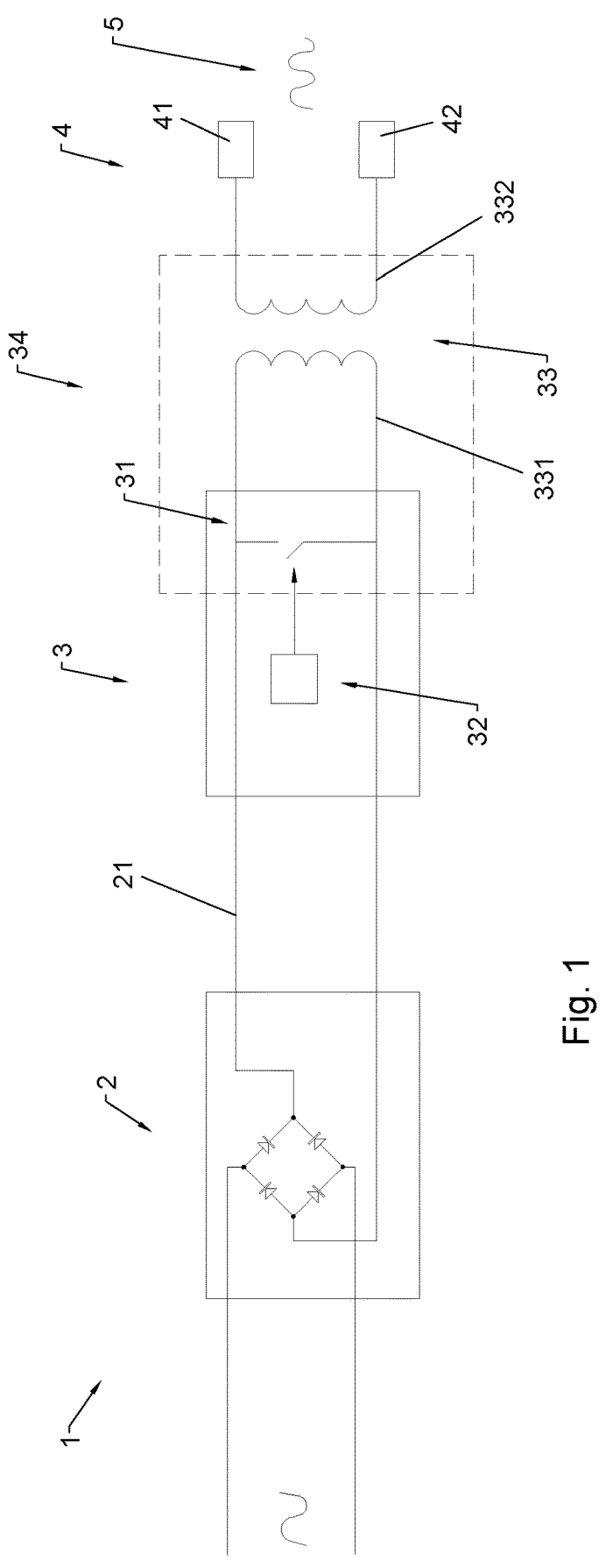
FIG. 1 schematically depicts the structure of an electronic device for biomedical use of the invention.

As mentioned above, in general, the electronic device for biomedical use of the invention, schematised in FIG. 1 and indicated overall by 1, according to the preferred embodiment of the invention, preferably but not necessarily, comprises a rectifier circuit 2 that can be preferably powered by a mains voltage or by any other alternating voltage source, such that the output voltage 21, at the output from said rectifier circuit 2 is preferably of a continuous type with a predetermined value, preferably comprised for example between 20V and 300V, even more preferably between 50V and 200V.

It is not excluded, however, that, according to embodiment variants of the invention, the electronic device for biomedical use 1 is not provided with a rectifier circuit 2, but it can be directly powered by a voltage preferably of a continuous type, generated for example by an electric battery.

Returning to the preferred embodiment depicted in FIG. 1, the device 1 is further provided with a radio frequency circuit 3 to which the rectifier circuit 2 supplies this output voltage 21 and at least one electrode 4, which is connected at the output to the radio frequency circuit 3 and is applicable on a person's body, in particular on the skin or on the internal tissues of said person.

Figure 2:
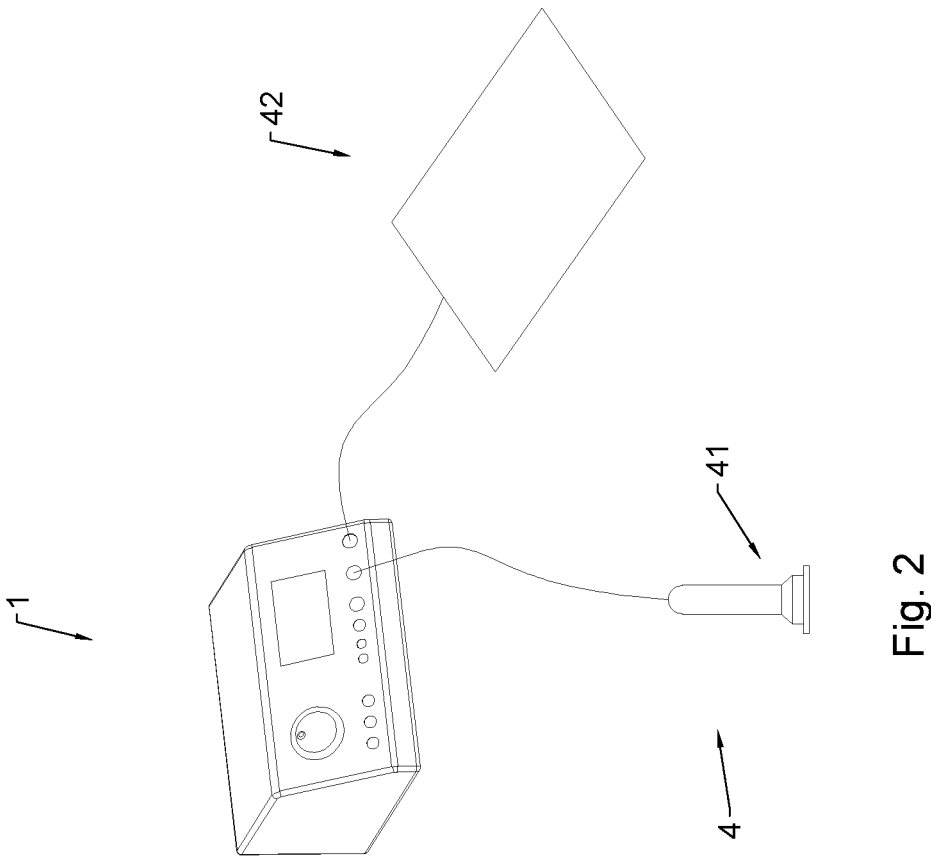
FIG. 2 schematically depicts a device of the invention to which two monopolar type electrodes are connected in order to close the electric circuit in contact with a person's body.

According to alternative embodiments for which the rectifier circuit 2 is not present, the aforesaid external voltage, preferably of a continuous type, is placed at the input to the radio frequency circuit 3. With regard to the electrode 4, it could preferably, but not exclusively, be a monopolar electrode 41 such as an insulated handpiece, a needle-shaped, a loop-shaped ball, or blade conductive electrode, a conductive glove or any type of electrode suitably shaped so that it can be brought into contact with a portion of a person's body. In this case, as schematised in FIG. 2, the device 1 preferably provides for the presence of a second return electrode 42 connected to the radio frequency circuit 3 in order, precisely, to close the electric circuit defined by the device and thus allow the current to flow through at least a portion of a person's body.

For example, in a non-limiting manner, said second return electrode 42 could have a flat surface in order to be placed into contact with the individual to be treated, so as to close the aforesaid electric circuit through the body of the aforesaid person.

It is not excluded, however, that said second electrode 42 may not be envisaged and the closing of the circuit is achieved by earthing.

Figure 3:
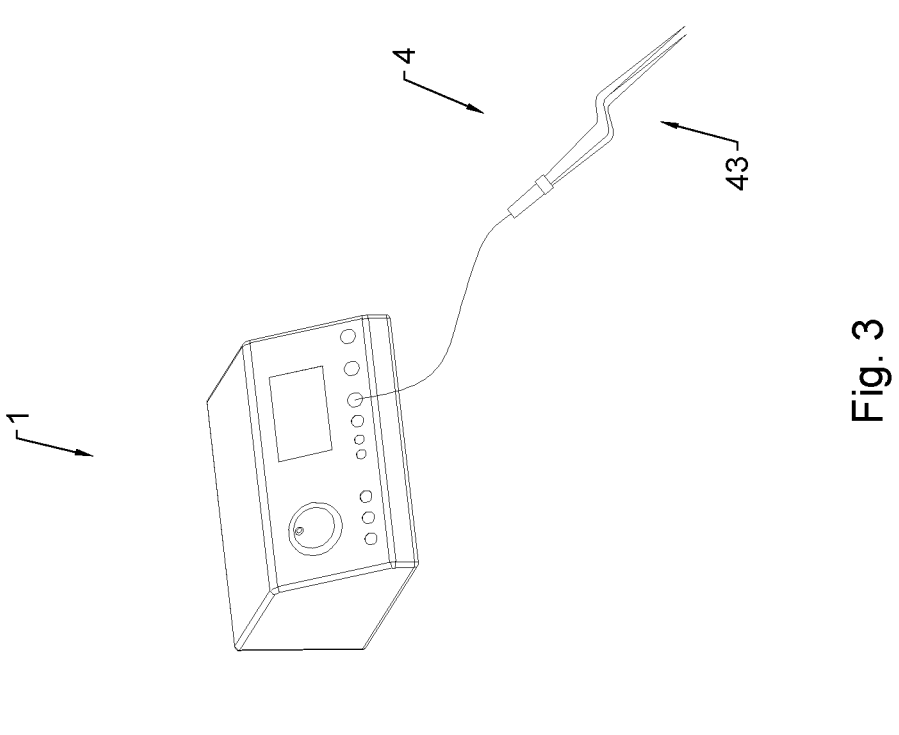
FIG. 3 schematically depicts a device of the invention to which a bipolar type electrode is connected in order to close the electric circuit in contact with a person's body.

Alternatively, as schematised in FIG. 3, said electrode 4 could be a bipolar type electrode 43, such as for example bipolar conducting forceps, bipolar scissors, bipolar clamps, each provided by definition with two poles isolated from each other, configured to close the electric circuit in contact with the human body.

Regarding, in particular, the radio frequency circuit 3, according to the invention, it is configured to generate as output an electric current wave 5 with fundamental frequency higher than or equal to 2 MHz and distorted by the presence of at least the second-order harmonic.

Preferably, but not necessarily, such an electric current wave 5 has a sinusoidal shape distorted by the presence of at least the aforesaid second-order harmonic.

Still preferably, this electric current wave has, as a fundamental frequency, a frequency comprised between 2 and 64 MHZ, specifically comprised between 2 and 16 MHz.

Even more preferably, the electric current wave generated by the radio frequency circuit 3 has, as a fundamental frequency, a frequency around 4 MHZ.

According to the invention, the radio frequency circuit 3 is configured such that the value of the percentage ratio, defined hereafter as the first percentage ratio, between the amplitude of the peak of the electric current wave 5 at the second-order harmonic and the amplitude of the peak of the electric current wave 5 at the fundamental frequency is comprised between 20% and 70%, when a load around 100 Ohms is applied to the electrode 4, and the same radio frequency circuit 3 is configured such that the value of the same first percentage ratio is comprised between 25% and 120%, when a load around 830 Ohms is applied to the aforesaid electrode 4.

In fact, the Applicant, as a result of experiments, has found that the appropriate variation in the value of this first percentage ratio, depending on the variation in the load applied to the device, within the above-mentioned ranges, allows the effect of the specific QMR treatment to be optimised depending on the tissue or cells to which this technology is applied.

Preferably, the aforesaid amplitudes of the peaks are equivalent to the value of the voltage V rms (root mean square) measured at the fundamental frequency and the relative second-order harmonics.

According to the invention, preferably but not necessarily, the radio frequency circuit 3 is also configured in such a way that the value of the aforesaid first percentage ratio is comprised between 25% and 95%, when a load around 430 Ohms is applied to the electrode 4.

This additional control of the value of the aforesaid first percentage ratio advantageously allows to further optimise the effect of the QMR treatment that is intended to be implemented.

Additionally, preferably but not necessarily, the radio frequency circuit 3 is configured in such a way that the electric current wave 5, generated by it, is also distorted by the presence of the third-order harmonic.

In this case, in particular, the radio frequency circuit 3 is configured in such a way that the value of the percentage ratio, defined below as the second percentage ratio, between the amplitude of the peak of the electric current wave 5 at the third-order harmonic and the amplitude of the peak of the current wave at the fundamental frequency is comprised between 2% and 60%, when a load around 100 Ohms is applied to the electrode 4, whereas this second percentage ratio is comprised between 4% and 120% when a load around 830 Ohms is applied to the same electrode 4.

Still, preferably but not necessarily, it is provided that the value of said second percentage ratio between the amplitude of the peak of the electric current wave 5 at the third-order harmonic and the amplitude of the peak of the current wave at the fundamental frequency is comprised between 2% and 90%, when a load around 430 Ohms is applied to the electrode 4, more preferably said second percentage ratio is comprised between 2% and 70% with said load of 430 Ohms.

Also in this case, the further control of the value of the peak of the electric current wave 5, at the third-order harmonic at the aforesaid three values of the load applied to the electrode 4 of the device 1, allows to further optimise the effect of the QMR treatment to be implemented.

Even more specifically, preferably, the radio frequency circuit 3 is also configured in such a way that the electric current wave 5, generated by it, also distorted by the presence of the fourth-order harmonic.

In this case, the value of the percentage ratio, defined below as the third percentage ratio, between the amplitude of the peak of the electric current wave 5 at the fourth-order harmonic and the amplitude of the peak of the current wave at the fundamental frequency is comprised between 0% and 40%, when a load around 100 Ohms is applied to the electrode 4, whereas the same third percentage ratio assumes a value comprised between 0% and 50%, when a load around 830 Ohms is applied to the same electrode 4.

Advantageously, still preferably but not necessarily, the aforesaid third ratio is comprised between 0% and 45%, even more preferably between 4% and 40%, when a load around 430 Ohms is applied to the electrode 4.

According to the preferred embodiment of the invention described herein, the radio frequency circuit 3 comprises an electronic switch 31 powered by said output voltage 21 and driven by an appropriate driving circuit 32.

Further, said radio frequency circuit 3 comprises, connected at the output to the aforesaid electronic switch 31, an electric transformer 33 so as to preferably define, with the same electronic switch 31, a resonant circuit 34 in a frequency band corresponding to the fundamental frequencies of the wave generated by the same radio frequency circuit 3.

It is not excluded, however, that, according to alternative embodiments of the invention, the radio frequency circuit 3, instead of including the aforesaid electronic switch 31, may comprise a different power electronic component, provided that it is capable of generating a current wave with the characteristics indicated above starting from the aforesaid output voltage 21.

Furthermore, still alternatively to the preferred embodiment described herein, the radio frequency circuit 3, instead of including the aforesaid electric transformer 33, could comprise a broadband filter suitably configured to allow the passage of an output current wave with the characteristics indicated above.

With regard to the configuration mode of the radio frequency circuit 3, in order to be able to obtain an electric current wave 5 with the characteristics indicated above at the output, it preferably envisages suitably configuring the electric/electronic components constituting said radio frequency circuit 3, in particular, the aforesaid electric transformer 33, and even more particularly, the number of the turns of the primary winding 331 and of the secondary winding 332 of the aforesaid transformer 33.

In an alternative embodiment of the invention, such a configuration mode could be achieved by suitably choosing the control software settings of the aforesaid driving circuit 32 of the electronic switch 31, in particular by suitably choosing, preferably but not necessarily, the percentage value of the duty cycle of the aforesaid driving circuit.

More precisely still, according to this latter embodiment of the invention, the electronic device for biomedical use 1, when in use, in particular when the electrode or the electrodes 4 is/are placed in contact with a part of a person's body, is configured to measure the impedance value of said part of the body, as seen by said device, in particular by the radio frequency circuit 3 and, based on the aforesaid impedance value, the device 1 of the invention is configured to modify, preferably but not necessarily, the aforesaid percentage value of the duty cycle, in order to generate an electric distorted current wave 5, having the characteristics indicated above depending on the impedance considered.

It is not excluded, however, that in a further embodiment variant it is provided to suitably configure both the aforesaid electric/electronic components, in particular the transformer 33, and the value of the duty cycle, in order to obtain an electric current wave 5 with the characteristics indicated above.

In addition, the device 1 of the invention is configured to allow the selection of the nominal electric power value that can be delivered, based on the treatment to be implemented. In particular, the device 1 is configured to allow the aforesaid nominal electric power value to be selected within a predetermined power range.

In particular, preferably but not necessarily, this power range is comprised between 0 Watts and 150 Watts of deliverable electric power, at the specific coupling impedance value.

It is necessary, at this point, to identify an unambiguous measurement protocol with which to determine the aforesaid values of the ratios between the amplitudes of the peaks of the various harmonics and the amplitude of the peak at the fundamental frequency.

First of all, it should be established that the measurements must be carried out by means of an oscilloscope O, preferably by means of an Agilent Infiniium DS09104A oscilloscope from the company Keysight Thechnologies or, alternatively, an equivalent oscilloscope, with the same functional and setting characteristics.

It is also envisaged to use a differential probe S, connected in the manner described shortly. In particular, it is preferable to use the KEYSIGHT N2891A differential probe. Also in this case, a similar differential probe with equivalent functional characteristics could be used.

Further, it is envisaged to use an impedance bank I with a plurality of resistors R suitable for operating within the range of frequencies indicated above, connectable in series, each with a given Ohmic value.

In particular, preferably, it is recommended to use the following resistors R to perform the above measurements:

ARCOL, FPA100 100R J with an Ohmic value of 100 Ohms;

ARCOL, FPA100 330R J with an Ohmic value of 330 Ohms;

ARCOL, FPA 1K J with an Ohmic value of 1000 Ohms;

OHMITE, TGHLV500RJE with an Ohmic value of 500 Ohms;

OHMITE, TGHHV50R0JE with an Ohmic value of 50 Ohms;

OHMITE, TGHLV25R0JE with an Ohmic value of 250 Ohms.

It is not excluded, however, that different types of resistors and/or different Ohmic values of the resistors may be used to perform the above measurements, provided that they are suitable for operating within the range of frequencies indicated above and that the Ohmic values indicated above can be defined as a load to be applied to the electrode 4 of the device 1.

Finally, for the connection of the measurement instruments introduced above and the device 1 of the invention, it is envisaged using electric cables C of 1 meter in length, preferably provided with "banana" connectors at the ends.

In particular, preferably the aforesaid cables C to be used could be flexible, polyurethane-coated bipolar cables with red copper conductors, with 0.25 mm2 cross-section for each conductor, with a maximum operating voltage of 250 V, electric resistance 100 Ohm/km and insulation test voltage 1500 V.

Also in this case, as an alternative, it cannot be ruled out that electric cables equivalent to those just described can be used.

Figure 4:
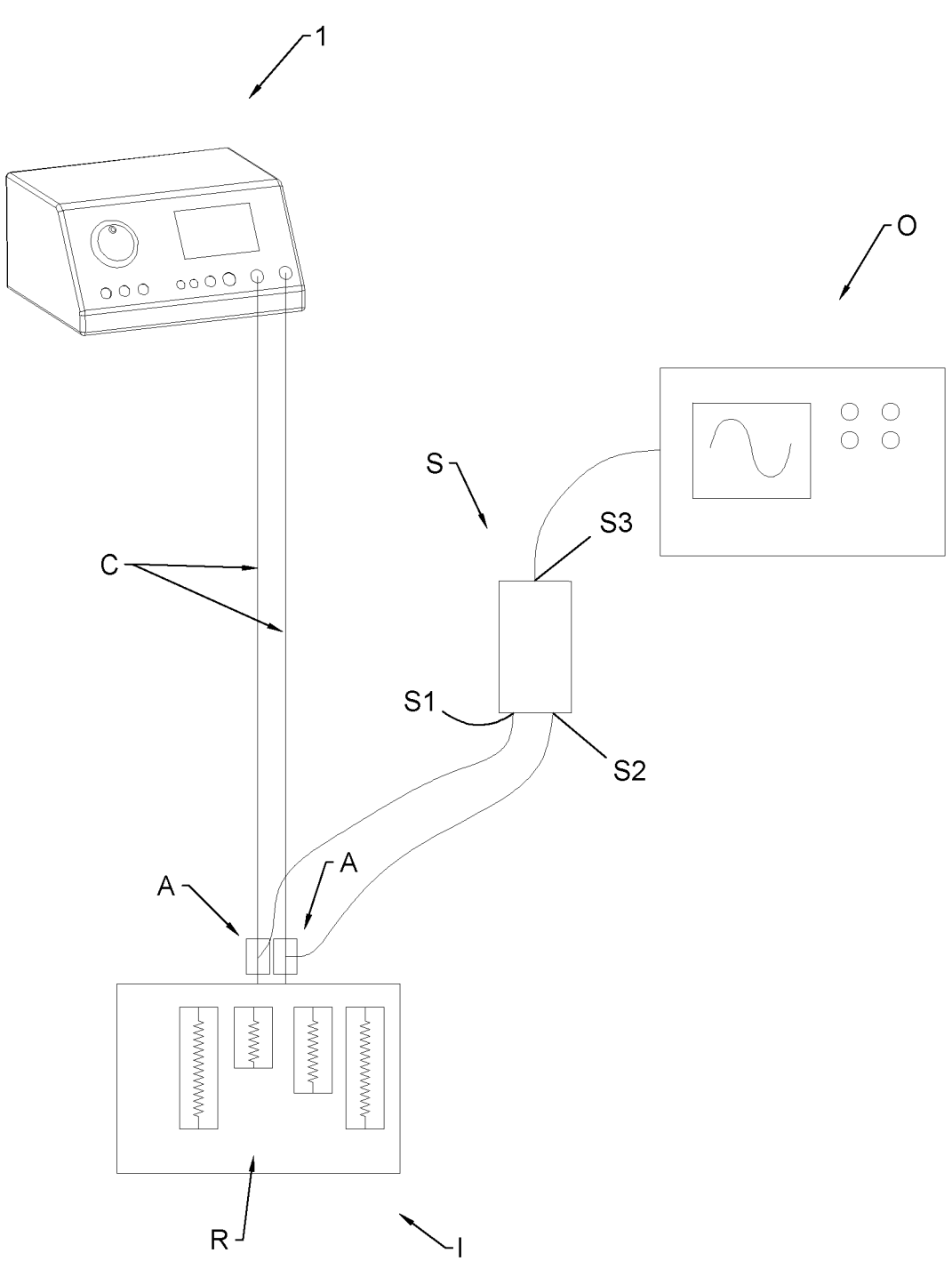
FIG. 4 depicts the diagram of connection of the measurement instruments to a device of the invention in order to measure the values of the amplitudes of the peaks of the electric current wave generated by the device, at the fundamental frequency and the harmonics.

With regard to the measurement setting, as schematically observed in FIG. 4, the cables C are to be connected to the output connectors of the device 1 of the invention, in particular, in the case of monopolar operating modes, to the neutral connector and to the phase connector to which the aforesaid electrodes 41 and 42 are normally connected. The cables C are to be arranged parallel to each other at a distance of approx. 50 cm.

In the case of bipolar operating mode, these cables C must be connected to the two poles of the bipolar connector of the device 1.

In this case, preferably, the aforesaid cables must be arranged parallel to each other at a minimum distance from one another, even more preferably they should belong to the same ribbon cable.

The opposite ends of the cables C are to be connected to the impedance bank I in order to define the overall Ohmic value of the load to be applied to the device 1 of the invention, this Ohmic value having been chosen at least from the three values indicated above, namely 100 Ohms, 830 Ohms and 430 Ohms.

The two inputs S1 and S2 of the differential probe S are to be connected between each of the aforesaid cables C and the impedance bank I.

Preferably, this connection is to be achieved by means of a three-way adapter A, interposed between each of these cables C and the impedance bank I.

The differential probe S must be set with an attenuation equal to $\frac{1}{100}$.

The differential probe S must be positioned as far away as possible from the measurement cables C in order not to be influenced by the signal to be measured.

The output S3 of the differential probe S must be connected to an input of the oscilloscope O.

The oscilloscope O must be set to perform the FFT (Fast Fourier Transform) analysis of the input electric current wave 5 and the measurement of the value DCV rms of the signal (i.e., the rms (root mean square) value of the signal without removing the continuous component) at the frequency of the fundamental one and of the second-order, third-order and fourth-order harmonics of the input electric current wave 5.

In addition, it is envisaged:

setting the Hanning filter for measuring the peaks of the harmonics;

activating the device 1 of the invention by setting a delivery power value within the range of values selectable by the same device 1;

acquiring the voltage values V rms at the fundamental frequency and at the harmonics, for each of the Ohmic load values indicated above, i.e., 100 Ohms, 830 Ohms and 430 Ohms.

From these acquired values, the values of the aforesaid first percentage ratio, second percentage ratio and third percentage ratio are calculated for each of the load values considered.

First Application Example

According to a first application example of the electronic device for biomedical use 1 of the invention, which is particularly suitable for use as a scalpel or for the treatment of musculoskeletal pathologies, eye pathologies, tinnitus, etc., it is configured in such a way that the fundamental frequency of the generated current wave is set to around 4 MHZ and that the aforesaid first percentage ratio is comprised between 35% and 65% when a load around 100 Ohms is applied to the electrode 4.

Furthermore, this first percentage ratio is comprised between 70% and 120%, when a load around 830 Ohms is applied to the electrode 4. More precisely, preferably but not necessarily, with a load of 830 Ohms, this first percentage ratio is comprised around 75% and 100%.

Further, preferably, said first percentage ratio is comprised between 70% and 90%, when a load around 430 Ohms is applied to this electrode 4, in particular, this first percentage ratio is comprised between 75% and 85%.

Again, preferably, according to this first application example, the second percentage ratio is comprised between 15% and 50%, when a load around 100 Ohms is applied to the electrode 4, and is comprised between 60% and 120%, when a load around 830 Ohms is applied to the electrode 4.

Preferably, but not necessarily, this second percentage ratio is comprised between 45% and 70%, when a load around 430 Ohms is applied to the electrode 4.

Furthermore, preferably but not necessarily, the third percentage ratio is comprised between 8% and 35% when a load around 100 Ohms is applied to the electrode 4, whereas it is comprised between 10% and 50% when a load around 830 Ohms is applied to the same electrode 4.

Furthermore, still preferably but not necessarily, the aforesaid third ratio is comprised between 10% and 45%, even more preferably between 15% and 40%, when a load around 430 Ohms is applied to the electrode 4.

The type of treatment for which the device 1 of the invention according to the aforesaid first application example is used, in addition to depending on the intrinsic characteristics just described, also depends on the type of electrode 4 that is chosen to be connected to the same device 1.

Second Application Example

A second application example of the electronic device for biomedical use 1 of the invention is particularly suitable mainly for aesthetic treatments, but also for musculoskeletal pathologies and inflammatory-degenerative pathologies. It is configured in such a way that the fundamental frequency of the generated current wave is set to around 4 MHz and that the aforesaid first percentage ratio is comprised between 15% and 45% when a load around 100 Ohms is applied to the electrode 4.

Moreover, this first percentage ratio is comprised between 25% and 50%, when a load around 830 Ohms is applied to the electrode 4. More precisely, preferably but not necessarily, with a load of 830 Ohms, this first percentage ratio is comprised between 30% and 45%.

Further, preferably, said first percentage ratio is comprised between 25% and 45%, when a load around 430 Ohms is applied to this electrode 4, in particular, this first percentage ratio is comprised between 28% and 40%.

Again, preferably, according to this second application example, the second percentage ratio is comprised between 1% and 10%, when a load around 100 Ohms is applied to the electrode 4, and is comprised between 1% and 15%, when a load around 830 Ohms is applied to the electrode 4.

Preferably, but not necessarily, this second percentage ratio is comprised between 1% and 15%, when a load around 430 Ohms is applied to the electrode 4. Furthermore, preferably but not necessarily, the third percentage ratio is comprised between 0% and 5%, when a load around 100

Ohms is applied to the electrode 4, whereas it is comprised between 0% and 5%, when a load around 830 Ohms is applied to the same electrode 4.

Furthermore, still preferably but not necessarily, the aforesaid third ratio is comprised between 0% and 5%, when a load around 430 Ohms is applied to the electrode 4.

The type of treatment for which the device 1 of the invention according to the aforesaid second application example is used, in addition to depending on the intrinsic characteristics just described, also depends on the type of electrode 4 that is chosen to be connected to the same device 1.

Based on the foregoing, therefore, the electronic device for biomedical use 1 of the invention achieves all the intended purposes.

In particular, the object of developing an electronic device adapted to generate a plurality of electric currents in the range of the QMR frequencies and also that is configured to modulate such currents depending on the cells and tissues to be treated and/or the biological effects to be obtained, and therefore depending on the Ohmic load applied to the device configured to generate such currents is achieved.

The object of realizing a device configured to generate such electric currents without simultaneously causing a thermal effect on the treated cells or tissues is also achieved.

Another object achieved is to realize a device that is configured to modify in real time and independently one or more of the parameters of the electric currents generated on the basis of the cellular or tissue response received, and therefore depending on the Ohmic load applied to the aforesaid electronic device.

The object of realizing a device with a good safety profile is also achieved.

Advantageously, the particular values of the aforesaid first percentage ratio, second percentage ratio, and third percentage ratio allow, advantageously, to modulate some of the biological effects obtained with the application of QMR, and therefore of the treatment that is intended to be carried out on the tissues or cells, even of a different type.

The invention claimed is:

1. An electronic device for biomedical use, comprising:
a radio frequency circuit which can be powered by a voltage;
at least one electrode connected at an output to said radio frequency circuit and applicable on a part of a person's body;
said radio frequency circuit being configured to generate as output an electric current wave with a fundamental frequency higher than or equal to 2 MHz and distorted by a presence of harmonics of at least a second order;
wherein a first percentage ratio between an amplitude of a peak of said electric current wave at said second-order harmonic and an amplitude of a peak of said electric current wave at said fundamental frequency is comprised between 20% and 70% when a load around 100 Ohms is applied to said at least one electrode, said first percentage ratio being comprised between 25% and 120% when a load around 830 Ohms is applied to said at least one electrode.

2. The device, according to claim 1, wherein said electric current wave has a distorted sinusoidal shape.

3. The device, according to claim 1, wherein said first percentage ratio is comprised between 35% and 65% when a load around 100 Ohms is applied to said at least one electrode and is comprised between 70% and 120% when a load around 830 Ohms is applied to said at least one electrode.

4. The device, according to claim 1, wherein said first percentage ratio between the amplitude of the peak of said electric current wave at said second-order harmonic and the amplitude of the peak of said electric current wave at said fundamental frequency is comprised between 70% and 90% when a load around 430 Ohms is applied to said at least one electrode.

5. The device, according to claim 4, wherein said first percentage ratio is comprised between 75% and 85% when a load around 430 Ohms is applied to said at least one electrode.

6. The device, according to claim 1, wherein said electric current wave is distorted also by a presence of a third-order harmonic, wherein a second percentage ratio between an amplitude of a peak of said electric current wave at said third order-harmonic and the amplitude of the peak of said electric current wave at said fundamental frequency is comprised between 2% and 60% when a load around 100 Ohms is applied to said at least one electrode, said second percentage ratio being comprised between 4% and 120% when a load around 830 Ohms is applied to said electrode.

7. The device, according to claim 6, wherein said second percentage ratio is comprised between 15% and 50% when a load around 100 Ohms is applied to said at least one electrode and is comprised between 60% and 120% when a load around 830 Ohms is applied to said at least one electrode.

8. The device, according to claim 6, wherein the second percentage ratio between the amplitude of the peak of said electric current wave at said third-order harmonic and the amplitude of the peak of said electric current wave at said fundamental frequency is comprised between 45% and 70% when a load around 430 Ohms is applied to said at least one electrode.

9. The device, according to claim 1, wherein said electric current wave is distorted also by a presence of a fourth-order harmonic, wherein a third percentage ratio between an amplitude of a peak of said electric current wave at said fourth-order harmonic and the amplitude of the peak of said electric current wave at said fundamental frequency is comprised between 0% and 40% when a load around 100 Ohms is applied to said at least one electrode, said percentage ratio being comprised between 0% and 50% when a load around 830 Ohms is applied to said at least one electrode.

10. The device, according to claim 9, wherein said third percentage ratio is comprised between 8% and 35% when a load around 100 Ohms is applied to said at least one electrode and is comprised between 10% and 50% when a load around 830 Ohms is applied to said at least one electrode.

11. The device, according to claim 9, wherein said third percentage ratio between the amplitude of the peak of said electric current wave at said fourth-order harmonic and the amplitude of the peak of said electric current wave at said fundamental frequency is comprised between 10% and 45% when a load around 430 Ohms is applied to said at least one electrode.

12. The device, according to claim 11, wherein said third percentage ratio is comprised between 15% and 40% when a load around 430 Ohms is applied to said at least one electrode.

13. The device, according to claim 1, wherein said fundamental frequency of said electric current wave is between 2 and 64 MHz.

\* \* \* \* \*